United States Patent [19]
Li et al.

[11] Patent Number: 6,136,799
[45] Date of Patent: Oct. 24, 2000

[54] COSOLVENT FORMULATIONS

[75] Inventors: Lukchiu Li, Vernon Hills; Edward Anthony Pec, Brookfield; Daniel H. Robinson, Lake Bluff; Dennis A. Stephens, Mt. Prospect, all of Ill.; Kathee Jantzi, Madison, Wis.; Thomas Barton May, Grayslake; John Paul Oberdier, Gurnee, both of Ill.

[73] Assignee: Abbott Laboratories, Abbott Park, Ill.

[21] Appl. No.: 09/057,143

[22] Filed: Apr. 8, 1998

[51] Int. Cl.⁷ .......................... A61K 31/59; A01N 45/00
[52] U.S. Cl. ............................... 514/167; 424/236
[58] Field of Search ................... 514/212, 424, 514/167; 424/236

[56] References Cited

U.S. PATENT DOCUMENTS

| | | | |
|---|---|---|---|
| 4,308,264 | 12/1981 | Udipi | 525/359.2 |
| 4,594,340 | 6/1986 | Partridge et al. | 514/167 |
| 4,855,294 | 8/1989 | Patel et al. | 514/212 |
| 5,098,899 | 3/1992 | Gilbert et al. | 514/167 |
| 5,502,224 | 3/1996 | Eugster et al. | 552/653 |
| 5,597,815 | 1/1997 | Deluca et al. | 514/167 |
| 5,629,302 | 5/1997 | Eugster et al. | 514/167 |

FOREIGN PATENT DOCUMENTS

| | | |
|---|---|---|
| 0416137 | 3/1991 | European Pat. Off. . |
| 0480572 | 4/1992 | European Pat. Off. . |
| 2260903 | 5/1993 | United Kingdom . |
| 9300079 | 1/1993 | WIPO . |
| 9636340 | 11/1996 | WIPO . |
| 97/37637 | 10/1997 | WIPO ............................ A61K 9/127 |

OTHER PUBLICATIONS

Bertino et al., Stability of an extemporaneous formulation . . . , American J. of Hosp. Pharmacy, V38(12), p. 1932–1933, 1981.

mortensen et al., Toxicity of 1,25–dihydroxyvitamin D3 . . . , Journal of Investigative Dermat . . . , V 1(1), p. 60–63, 1996.

Whittle et al., Intravenous vitamin D in the detection of . . . , The Lancet, vol. 1, pp. 747–750, (1969).

Bertino et al., Stability of an extra . . . , American J. of Hosp. Pharmacy, vol. 38/12, pp. 1932–1933, (1981).

*Primary Examiner*—Marianne M. Cintins
*Assistant Examiner*—Vickie Kim
*Attorney, Agent, or Firm*—Gregory W. Steele

[57] ABSTRACT

Stable pharmaceutical formulations of a therapeutic agent, a low molecular weight alcohol and a glycol derivative are disclosed. Preferred formulations include 19-nor-1α,3β,25-trihydroxy-9,10-secoergosta-5,7(E),22(E)-triene.

14 Claims, 3 Drawing Sheets

COSOLVENT FORMULATIONS

BACKGROUND OF THE INVENTION

1. Field of the Invention

This invention relates to cosolvent formulations for therapeutic agents, the formulations having a synergistic preservative effect.

2. Discussion of the Prior Art

There is a continuing need to develop efficacious formulations for therapeutic agents that offer advantages in manufacturing, processing and safety for the patient. In particular, many therapeutic agents, for example vitamin D compounds, are oxygen sensitive or are otherwise unstable. Thus, the need to protect such compounds has lead to the routine addition of antioxidants in order to preserve the integrity of the active agent. In other formulations, buffers may be necessary to maintain pH. Chelating agents, including but not limited to citric acid, tartaric acid, amino acids, thioglycolic acid, and edetate disodium (EDTA), and buffers, including but not limited to acetate, citrate, glutamate, and phosphate buffers, are often used to stabilize formulations. However, as discussed in WO 96/36340, buffers and chelating agents have been implicated in imparting aluminum levels in products to in excess of 3.5 parts per million at the expiration date of the product.

It would be particularly advantageous to minimize aluminum levels in formulations for parenteral administration for patients on dialysis to minimize the risk of aluminum accumulation as these patients may develop osteomalacia. Potential adverse effects of EDTA may also include nephrotoxicity and renal tubular necrosis. Furthermore, EDTA is a chelating agent that is not an approved excipient in some international markets, such as Japan.

The present invention provides a formulation that overcomes these and other problems associated with pharmaceutical formulations. The present invention provides a formulation that requires no antioxidant, contains no additives that would lead to an increase in the levels of aluminum in the formulation, and may be terminally sterilized. It has also been surprisingly discovered that the novel formulations of the invention provide a synergistic preservative effect that could not be predicted from the anti-microbial effect of the alcohol and gylcol derivative as individual agents.

SUMMARY OF THE INVENTION

The present invention provides a pharmaceutical composition comprising a therapeutically effective amount of a therapeutic agent and an organic solvent selected from low molecular weight alcohols and glycol derivatives. The formulations of the invention provide a synergistic preservative effect. The term "synergistic preservative effect" means a preservative effect that is not additive, as would be predicted from the individual effect of each agent, but is instead gives a level of preservation which is above that which would be predicted, i.e., is synergistic. The preservative effect is measured following the guidelines of USP 23.

Preferred embodiments provide compositions comprising vitamin D compounds, ethanol and propylene glycol (PG). More preferred are compositions comprising paracalcitol, ethanol, propylene glycol and further comprising water. Most preferred are compositions comprising paracalcitol, 20% (v/v) ethanol, 30% (v/v) PG, and 50% (v/v) water.

A further embodiment of the invention provides a solution that is suitable to provide a synergistic preservative effect to therapeutic agents dissolved therein.

A further embodiment of the invention provides terminally sterilized formulations of the present invention.

Yet another embodiment of the present invention is a formulation which provides a final dosage form of paracalcitol which contains 5 μg/ml paracalcin, ethanol, propylene glycol, and water.

Processes for preparing such sterile, cosolvent solutions are also disclosed.

DETAILED DESCRIPTION OF THE INVENTION

Figure 1:
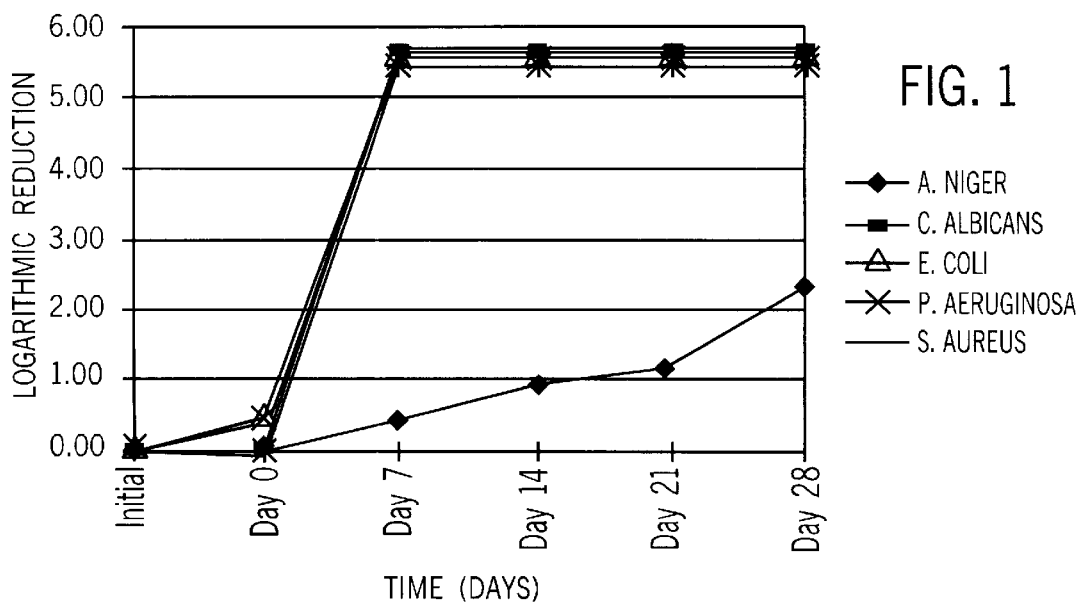
FIG. 1 shows the preservative effectiveness of a 20% (v/v) ethanol solution.

The present invention provides a self-preserved, stable, formulation of a therapeutic agent in a cosolvent formulation.

The therapeutic agent which can be utilized with the formulations of the present invention may be selected from the entire range of biologically and/or pharmacologically active substances which lack adequate solubility in aqueous systems, that is, agents which lack adequate solubility in water to yield an effective therapeutic dose. The precise biological activity of the substance is immaterial so long as the substance can be dissolved in the present formulations. More preferred are agents which are soluble at less than 1 μg/ml in water. Preferred agents of this subclass are vitamin D compounds, for example, calcitriol and paracalcitol.

The preferred route of administration of the formulations of the present invention is parenteral, most preferred is intravenous.

The term "vitamin D compound" means vitamin D and its derivatives. Exemplary vitamin D compounds are 19-nor-1α,3β,25-trihydroxy-9,10-secoergosta-5,7(E),22(E)-triene (generic name paracalcitol) and 1α,25-dihydroxycholecalciferol (generic name calcitriol).

The term "low molecular weight alcohol" means an aliphatic alcohol of from 1 to 5 carbons, e.g., ethanol, propanol, butanol, etc. Ethanol is listed on the United States Food and Drug Administration's (FDA) list of compounds, which are generally recognized as safe (GRAS), and is therefore preferred in formulations of the present invention intended for administration to humans.

The term "glycol derivative" refers to liquid or solid compounds e.g., glycerin, as well as polymers of glycol, e.g., polyethylene glycol (PEG) and propylene glycol (PG). Preferred for parenteral administration are liquid polymers, typically having molecular weight less than 1,000. The most preferred glycol derivative is PG.

Unless specified to the contrary, the percent concentrations stated herein are on a volume per volume (v/v) basis.

The organic solvent may comprise up to 100% of the excipient in the compositions of the present invention. It will be appreciated by those skilled in the clinical arts that the amount of organic solvent in the preferred parenteral formulations of the invention should be kept to a minimum. At the same time the requirements of manufacturing and required dosage ranges must be considered to ensure adequate solubility of the vitamin D compound in the present formulations.

Thus, the amount of low molecular weight alcohol may range from zero to 100%, keeping in mind that greater than 50% alcohol may present added expense and difficulties in manufacturing. The preferred range is about 15 to about 50% with the preferred alcohol being ethanol. When the therapeutic agent is paracalcitol, the most preferred are solutions containing 20% ethanol.

The amount of glycol derivative may also vary from zero to 100%. The preferred range is about 15 to about 35%. When the therapeutic agent is paracalcitol, the preferred glycol derivative is propylene glycol at 30%.

When the total amount of organic solvent comprises less than 100% of the volume, the remainder can be made up with water. As it is preferred that the total amount of organic solvent in preparations for parenteral administration be kept to a minimum, the preferred amount of water is 50%.

Thus, the most preferred formulation of the present invention contains about 15 to about 50% ethanol, about 15 to about 50% FPG, and the balance, if needed, water.

The amount of the therapeutic agent in the formulations of the invention is dependent merely on the solubility of the agent in the excipients of the present invention. Those skilled in the art can, without undue experimentation, determine the solubility of any therapeutic agent in the compositions described herein.

The amount of the therapeutic agent is not critical to the present invention and may be varied so as to obtain an amount of the agent that is effective to achieve the desired therapeutic response for a particular patient, composition, and mode of administration. The selected dosage level will depend on the activity of the therapeutic agent, the route of administration, the severity of the condition being treated and the condition and prior medical history of the patient being treated. The preferred therapeutic dose for the preferred vitamin D compounds is between about 2 and about 10 $\mu$g/ml, 5 $\mu$g/ml being most preferred.

The cosolvent formulations of the present invention provide certain advantages over prior art formulations.

With respect to lipid based formulations of the prior art, the formulations of the present invention are more readily manufactured, both in ease of manufacture and in the omission of steps to prevent peroxide formation in the resulting formulation, and may be more readily tolerated by patients for whom excess lipid exposure is a concern.

In addition, the formulations of the present invention omit the use of surfactants, which can cause irritation at the site of injection in some patients. The formulations of the present invention also avoid the use of buffering agents in order to control the pH of the solution. This is an additional advantage in manufacturing and provides a further advantage of avoiding the source of aluminum in the finished formulation. In addition, the present formulations do not suffer from discoloration due to the use of antioxidants, as such excipients are not required. Thus while buffers, surfactants and additional excipients may be added to the present formulation, such additional components are not critical to achieve the self-preserving feature or to maintain the stability of the therapeutic agents therein.

A further advantage of the formulations of the present invention is that the formulations may be terminally sterilized. With respect to formulations, terminal sterilization generally includes, but is not intended to be limited to, autoclaving, gamma radiation and electron beam sterilization techniques. For purposes of this disclosure, terminal sterilization will primarily refer to autoclaving processes. Of course, aseptic fill techniques may also be employed, however, terminal sterilization is preferred.

Terminal sterilization provides greater sterility assurance level (SAL) ($10^{-6}$), than that of aseptic filling ($10^{-3}$). Thus, terminal sterilization of the formulations of the present invention, sterilized by autoclaving, imparts a $10^3$ fold increase in SAL of the final product over aseptic filling techniques. Parenteral products manufactured having a high SAL reduce patient exposure to potential infections.

It has been surprisingly discovered that the formulations of the present invention provide yet another advantage over prior art formulations. Ethanol is well known for being a bactericidal and fungicidal agent, although ordinary use would involve ethanol at a concentration in excess of 70%. Ethanol is not used as a preservative per the definition of USP 23 and is not listed as preservative in any drug formulation listed in Physicians Desk Reference (1995). Propylene glycol has been defined as a true preservative and at least one formulation has used this solvent at a concentration of 3%. We have discovered that combinations of these preferred solvents provide an antimicrobial effect greater than that which would be predicted from the additive effect of the solvents. In particular it was discovered that the synergistic effect is observed with respect to at least three of the organisms that are used in the well-recognized test USP 23.

Thus, yet a further advantage provided by the formulations of the present invention is in the ability to package therapeutic agents in packaging, e.g., vials, which are suitable for multiple use.

In the most preferred embodiments of the invention, a paracalcitol formulation for parenteral administration may be supplied in a sterile unit dose flint glass vial or ampoule of 1, 2, or 5 ml. The dosage forms are stable for extended periods and can be stored at temperatures of from about 15° to 30° C.

Each 1 ml of solution preferably contains 5 $\mu$g of paracalcitol, 0.2 ml ethanol, 0.3 ml PG, and water for injection q.s.

It is understood by those skilled in the art that all components of the present formulations are of a pharmaceutically acceptable grade and quality.

Ampoules or vials containing the formulations of the present invention may be aseptically filled using a series of filters to assure a sterility assurance level (SAL) of $1\times10^{-3}$. More preferably, ampoules or vials containing the formulations of the present invention may be filled and then terminally sterilized to provide a SAL of $1\times10^{-6}$. For example, a solution of a formulation of the present invention may be filtered, using a 0.45 micrometer ($\mu$m) or finer membrane filter (Millipore Corporation, Bedford, Mass. 01730), into ampoules. The containers may be sealed and terminally sterilized.

Terminal sterilization of the final product may be done under conditions that are suitable to maintain the stability of the product. Preferably, the formulations are terminally sterilized at an $F_0$ of about 8 to about 18. The term "$F_0$" means the integrated lethality or equivalent minutes at 121.11° C. and is well known to those skilled in the art. For example, a $F_0$ of 8 denotes a sterilization cycle run at 121.11° C., with saturated steam for 8 minutes, while a $F_0$ of 18 denotes a cycle at 121.110° C., with saturated steam for 18 minutes.

EXAMPLE 1
Solubility of Paracalcitol in a Cosolvent System

An adequate amount of paracalcitol was weighed and added to 10 ml of cosolvent contained in a 10 ml stoppered glass test tube. Two samples were prepared for each cosolvent composition. The test tubes containing samples were shaken in a 25° C. reciprocal shaking water bath at 100 rpm. Upon complete dissolution, an aliquot was filtered through a 0.45 micron syringe filter and the filtrate diluted 1:1 with 50% methanol. The resulting diluted material was measured for the content of paracalcin. Table 1 shows the results of concentration of paracalcin in the listed cosolvent systems.

TABLE 1

| Ethanol | Propylene glycol | Water | Percalcitol (µg/ml) |
| --- | --- | --- | --- |
| 0.00 | 0.506 | 0.494 | 14.21 |
| 0.00 | 0.302 | 0.698 | 0.58 |
| 0.100 | 0.257 | 0.643 | 2.88 |
| 0.199 | 0.207 | 0.594 | 15.94 |
| 0.201 | 0.308 | 0.491 | 72.90 |
| 0.299 | 0.00 | 0.701 | 6.82 |
| 0.347 | 0.102 | 0.551 | 119.37 |
| 0.498 | 0.00 | 0.502 | 601.63 |

EXAMPLE 2
Stability of Paracalcitol in a Cosolvent Formulation

Samples of paracalcitol (5 µg/ml) in 20% ethanol/30% propylene glycol/50% water were prepared for stability testing. In an appropriate vessel, water for injection to approximately 30% of final volume is added. Propylene glycol is added to the vessel with mixing. In a separate container, the specified amount of paracalcitol is dissolved in a portion of the ethanol (190 proof non-beverage), which is obtained from the total volume of ethanol specified for the batch, and added to the vessel with mixing. An additional aliquot of the batch ethanol is used to rinse the container and the rinsing solution is added to the vessel with mixing. The remaining alcohol is added to the vessel with mixing. Q.s. with water for injection to final volume and mix for approximately 30 minutes. The solution is filtered through a 0.45 micron membrane and dispensed into ampuls. Each ampul is flame sealed and autoclaved to $F_0$ 16.

One set of ampuls are tested (T=0) for percent paracalcitol remaining in solution and served as control (i.e., 100% remaining). A second set of ampuls are stored at 40° C. and tested at 1, 2, and 3 months. A final set are stored at 30° C. and tested at 1, 2, 3, 6, 9, 12, 18, and 24 months. The results are shown in Table 2 as paracalcin remaining as a percent of control (T=0). Each time point represents 1 to 5 data points.

TABLE 2

| Time (months) | 30° C. | 40° C. |
| --- | --- | --- |
| 0 (Initial) | 100 | 100 |
| 1 | 96 | 96 |
| 2 | 96 | 96 |
| 3 | 97 | 98 |
| 6 | 96 | n.t. |
| 9 | 97 | n.t. |
| 12 | 100 | n.t. |

TABLE 2-continued

| Time (months) | 30° C. | 40° C. |
| --- | --- | --- |
| 18 | 97 | n.t. |
| 24 | 96 | n.t. |

EXAMPLE 3
Self-preserved Cosolvent Formulations

Solutions of 20% ethanol, 30% propylene glycol, 20% ethanol/30% PG, 30% ethanol/20% PG, and 40% ethanol/10% PG were passed through a 0.45 micron filter and tested by the USP 23 preservative effectiveness test as described in United States Pharmacopoeia 23-NF 18, 1995 Ed., Chapter 51, page 1681, which is incorporated herein by reference. Briefly, this involves inoculating the test solution with $10^5$ to $10^6$ test organisms per milliliter and then determining the number of surviving organisms after 7, 14, 21, and 28 days incubation at 20–25° C. using standard microbiological methods. Day 0 data is not required by USP 23 but was included in this study. A filtration and wash method was used to remove the inactivating agents for purposes of recovering the microorganisms, but other equivalent methods can also be validated for use. The USP test organisms include the bacteria *Staphylococcus aureus, Escherichia coli,* and *Pseudomonas aeruginosa,* a yeast (*Candida albicans*), and a mold (*Aspergillus niger*). In order to meet the criteria of the USP 23 preservative effectiveness test, the bacteria must demonstrate a 90% (1 logarithmic) reduction at Day 7 and a 99.9% (3 logarithmic) reduction at Day 14 from the initial inoculum level. The yeast and mold must not increase from the initial inoculum level. The initial inoculum level can either be calculated by knowing the stock culture concentration or by using a buffer control instead of the test solution.

Figure 2:
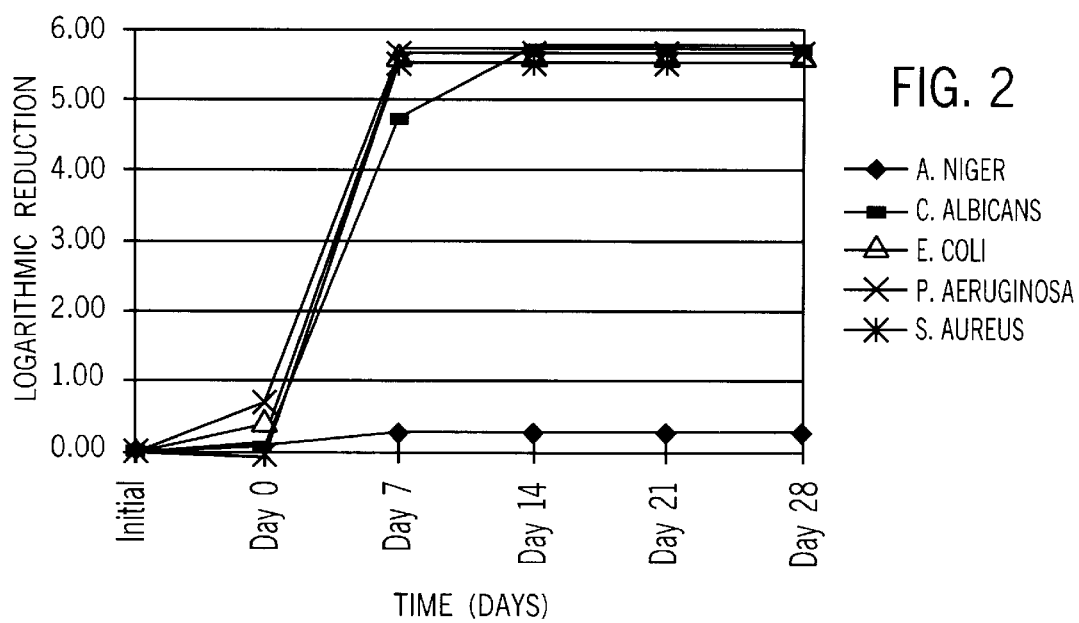
FIG. 2 shows the preservative effectiveness of a 30% (v/v) propylene glycol solution.

As can be seen by reference to FIGS. 1 and 2, both the solution of 20% ethanol and 30% propylene glycol meet the acceptance criteria of the USP 23 preservative effectiveness test. With respect to the mold *Aspergillus niger,* it is noted that neither solvent provides complete elimination of the microorganism; 20% ethanol is inhibitory and 30% PG has very little effect. As stated above, this result are not entirely unexpected as both of these solvents are recognized in the art as antimicrobial agents.

Figure 3:
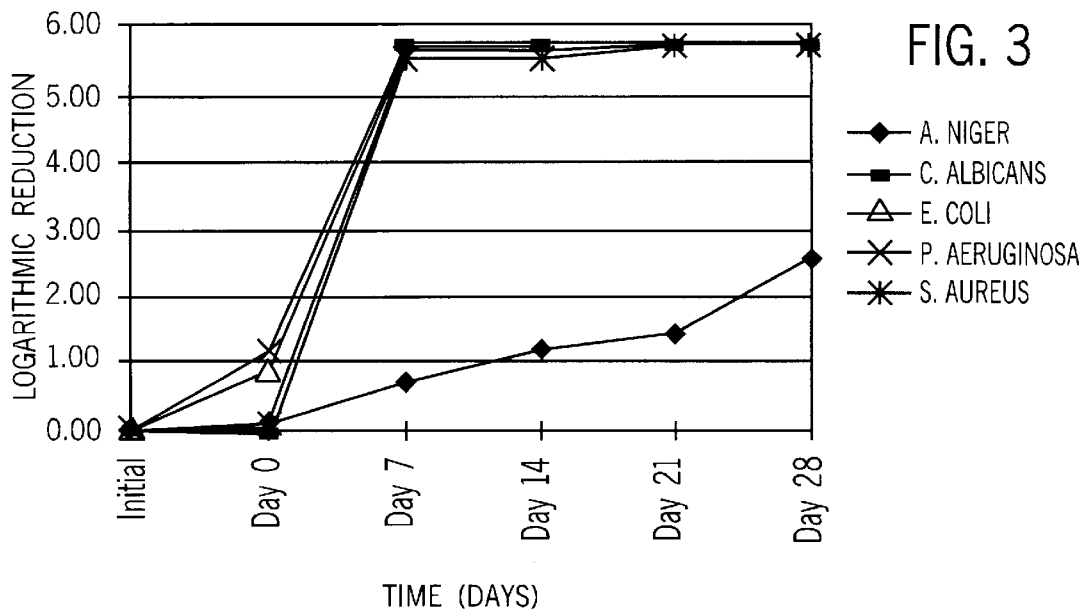
FIG. 3 shows the predicted preservative effectiveness of a 20% (v/v) ethanol/30% (v/v) propylene glycol solution.
Figure 4:
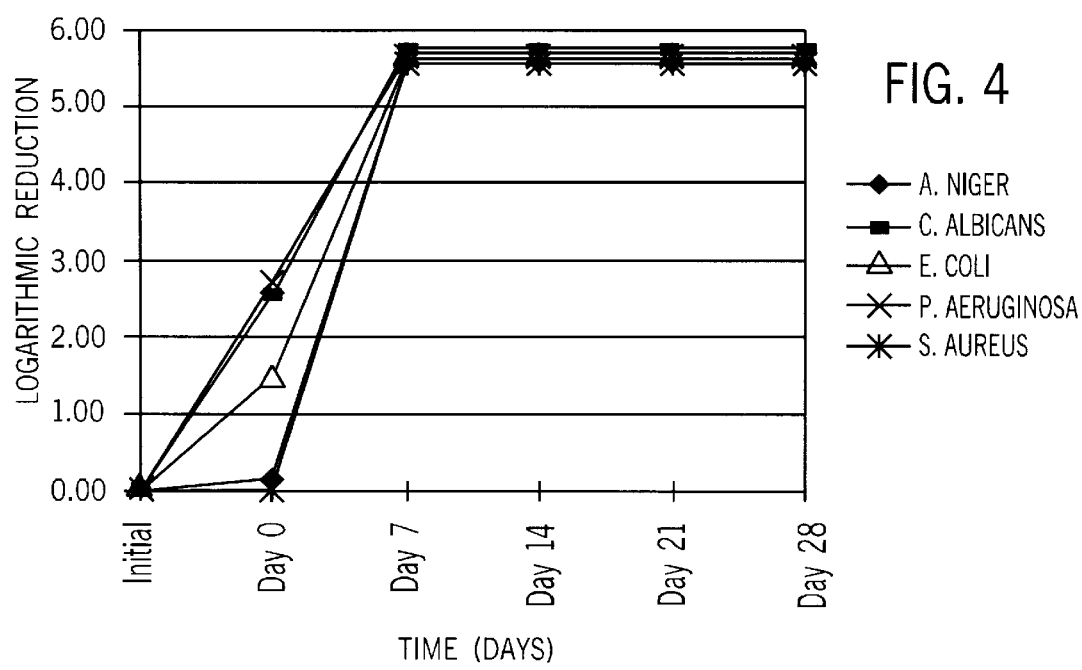
FIG. 4 shows the actual preservative effectiveness of a 20% (v/v) ethanol/30% (v/v) propylene glycol solution.

As both propylene glycol and alcohol share antimicrobial and solvent properties, the preservative effect of this cosolvent system would be predicted to be sum of the individual efficacies of ethanol and propylene glycol (H. Takruri and C. B. Anger, Preservation of Dispersed Systems, pp. 85, 101 in Pharmaceutical Dosage Forms; Dispersed Systems, H. A. Lieberman, M. M. Reiger, and G. S. Banker, Ed. (1989)). FIG. 3 shows this predicted effect of a solution of 20% ethanol in combination with 30% propylene glycol, as determined by the sum of values generated for FIGS. 1 and 2. However, FIG. 4 shows the unexpected result of the actual preserving effect that a combination of 20% ethanol and 30% propylene glycol is not additive, but is synergistic. The mold, *A. niger,* is completely killed, i.e., the number of microorganisms remaining is below the detection limits of the assay, by the cosolvent within the 7 days. The addition of paracalcin to the 20% ethanol/30% PG formulation has no effect on the preservative effect of the formulation (data not shown).

Figure 5:
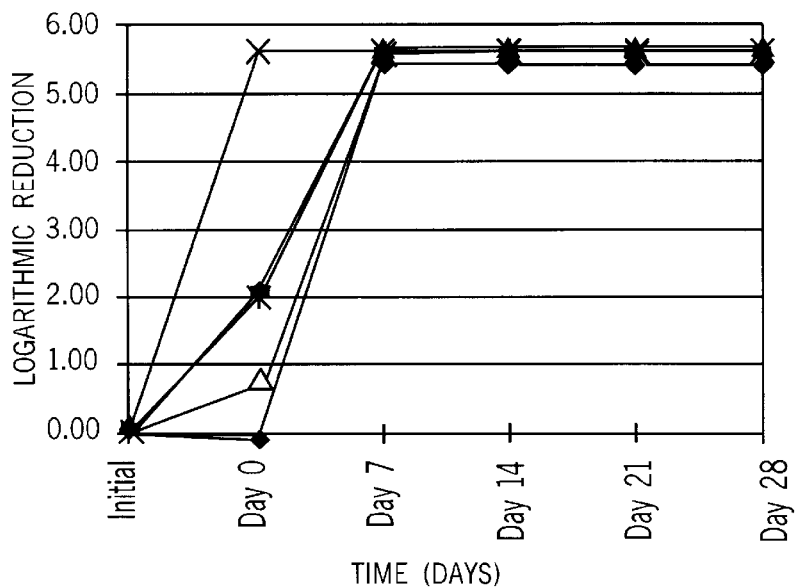
FIG. 5 shows the preservative effectiveness of a 30% (v/v) ethanol/20% (v/v) propylene glycol solution.
Figure 6:
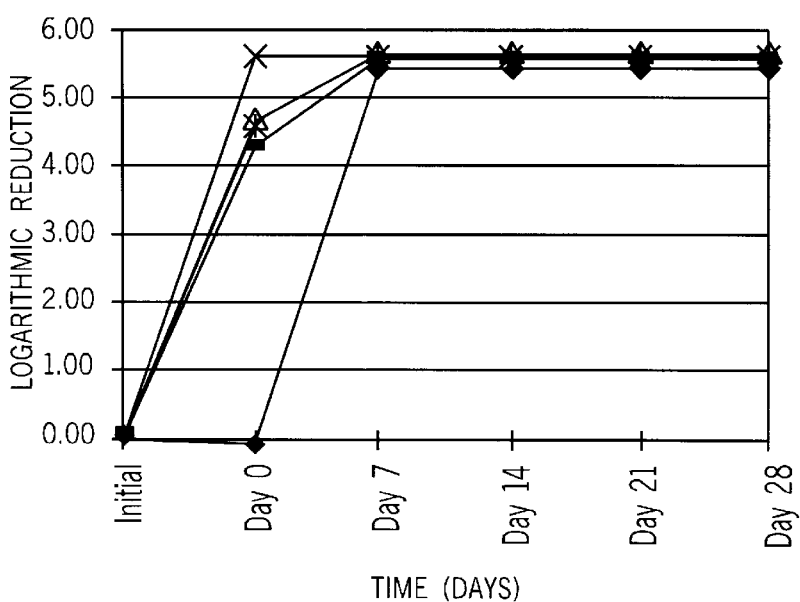
FIG. 6 shows the preservative effectiveness of a 40% (v/v) ethanol/10% (v/v) propylene glycol solution.

FIGS. 5 and 6 demonstrate that the ratio of ethanol and PG is not critical to the self-preserving properties of this cosolvent formulation.

We claim:

1. A sterilized, self-preserved, aqueous pharmaceutical composition for parenteral administration consisting essentially of a therapeutically effective amount of a vitamin D compound, about 50% (v/v) of an organic solvent selected from the group consisting of low molecular weight alcohols in the range of about 15% to about 30% (v/v) and glycol derivatives in the range of about 20% to about 35% (v/v), and about 50% (v/v) water.

2. The composition of claim 1 wherein the low molecular weight alcohol is ethanol.

3. The composition of claim 1 wherein the glycol derivative is selected from the group consisting of glycerin and propylene glycol.

4. The composition of claim 3 wherein the glycol derivative is propylene glycol.

5. The composition of claim 1 wherein the vitamin D compound is selected from the group consisting of parecelcitol and calcitriol.

6. The composition of claim 1 wherein the low molecular weight alcohol is ethanol and the glycol derivative is propylene glycol.

7. The composition of claim 6 wherein the vitamin D compound is paracalcitol or calcitriol.

8. The composition of claim 7 wherein the vitamin D compound is present between about 2 µg/ml and about 10 µg/ml.

9. The composition of claim 8 wherein the vitamin D compound is present at about 5 µg/ml.

10. The formulation of claim 1 wherein sterilization is terminal sterilization.

11. The formulation of claim 1 wherein the sterilization is aseptic fill.

12. A sterilized, self-preserved pharmaceutical formulation for parenteral administration consisting essentially of:

2–10 micrograms/milliliter of a paracalcitol;

20% (v/v) ethanol;

30% (v/v) propylene glycol; and

50% (v/v) water.

13. A process for preparing a pharmaceutical formulation comprising a therapeutically effective amount of paracalcitol comprising the steps of:

a) preparing a mixture of water and propylene glycol;

b) preparing a mixture of paracalcitol and ethanol;

c) combining the mixtures from steps (a) and (b) to prepare a uniform mixture; and d) filtering said uniform mixture.

14. A unit dose of a sterile, self-preserved pharmaceutical formulation for parenteral administration consisting essentially of:

2–10 micrograms/milliliter of paracalcitol;

20% (v/v) ethanol;

30% (v/v) propylene glyco; and

50% (v/v) water.

* * * * *

UNITED STATES PATENT AND TRADEMARK OFFICE
CERTIFICATE OF CORRECTION

PATENT NO.   : 6,136,799
DATED        : October 24, 2000
INVENTOR(S)  : Lukchiu Li et al.

It is certified that error appears in the above-identified patent and that said Letters Patent is hereby corrected as shown below:

Column 2,
Line 5, replace "paracalcin" with -- paracalcitol --.

Column 3,
Line 26, replace "FPG" with -- PG --.

Column 4,
Line 63, replace "$F^0$" with -- $F_0$ --.

Column 5,
Line 1, replace "121.110°" with -- 121.11° --.
Line 14, replace "paracalcin." with -- paracalcitol. --.
Line 15, replace "paracalcin" with -- paracalcitol --.

Column 6,
Line 63, replace "paracalcin" with -- paracalcitol --.

Column 7,
Line 8, replace "parecelcitol" with -- paracalcitol --.

Signed and Sealed this

Ninth Day of September, 2003

JAMES E. ROGAN
*Director of the United States Patent and Trademark Office*